United States Patent [19]

Zondler et al.

[11] Patent Number: 4,718,934
[45] Date of Patent: Jan. 12, 1988

[54] 5-ACYLAMINOPYRIMIDINES

[75] Inventors: Helmut Zondler, Bottmingen; Hans Tobler, Allschwil; Urs Müller, Münchenstein, all of Switzerland

[73] Assignee: Ciba-Geigy Corporation, Ardsley, N.Y.

[21] Appl. No.: 853,308

[22] Filed: Apr. 17, 1986

Related U.S. Application Data

[63] Continuation-in-part of Ser. No. 775,971, Sep. 13, 1985, abandoned.

[30] Foreign Application Priority Data

Sep. 20, 1984 [CH]  Switzerland .................. 4495/84
Jun. 5, 1985 [CH]  Switzerland .................. 2382/85

[51] Int. Cl.$^4$ .................. A01N 43/54; C07D 239/50
[52] U.S. Cl. .................. 71/76; 71/92; 544/322; 544/331
[58] Field of Search .................. 544/322, 331; 71/76, 71/92

[56] References Cited

U.S. PATENT DOCUMENTS 4,552,960 11/1985 Krumkalns et al. ............... 544/296

FOREIGN PATENT DOCUMENTS 3331873 3/1984 Fed. Rep. of Germany .

OTHER PUBLICATIONS

Minagawa, et al., "Chemical Abstracts", vol. 72, 1970, col. 67723t.
Krumkalns, et al., (II), "Chemical Abstracts", vol. 103, 1985, col. 103:6367s.
Milzner, et al., "Chemical Abstracts", vol. 701, 1984, col. 101:90959a.

*Primary Examiner*—Glennon H. Hollrah
*Assistant Examiner*—James H. Turnipseed
*Attorney, Agent, or Firm*—Edward McC. Roberts

[57]  ABSTRACT

The invention relates to novel 5-acylaminopyrimidines of the general formula I

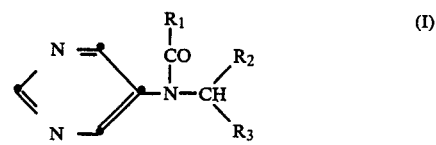

wherein
$R_1$ is lower alkyl, lower alkoxy, lower alkoxy-lower alkyl, thioalkyl or halogen; phenyl or phenoxy, each unsubstituted or substituted by halogen, halo-lower alkyl, carbalkoxy-lower alkyl, halo-lower alkoxy, lower alkoxy, phenoxy, halophenoxy, halo-lower alkylthio, cyano or nitro; lower alkenyl or lower alkynyl, or unsubstituted or substituted cycloalkyl
$R_2$ is lower alkyl which is unsubstituted or substituted by halogen, cyano or lower alkoxy; phenyl or phenyl-lower alkyl, each unsubstituted or substituted; pyridyl, thienyl or furyl, in which the nucleus is unsubstituted or substituted, or is pyranyl, dihydropyranyl, $C_3$–$C_7$cycloalkyl or $C_3$–$C_7$alkenyl, and
$R_3$ is hydrogen or $C_1$–$C_8$alkyl and $R_2$ and $R_3$, together with the carbon atom to which they are attached, may form a cycloalkyl radical, which compounds are effective as plant growth regulators. The invention relates further to compositions which contain at least one of these compounds as active ingredient, and to the use thereof, as well as to the corresponding novel 5-aminopyrimidines and, as intermediates, to the novel azomethines from which they are obtained.

18 Claims, No Drawings

5-ACYLAMINOPYRIMIDINES

This application is a continuation-in-part of application Ser. No. 775,971 filed Sept. 13, 1985, now abandoned.

The present invention relates to novel 5-acylaminopyrimidines as plant growth regulators, to compositions which contain at least one of these compounds as active ingredient and to the use thereof.

The present invention accordingly provides novel 5-acylaminopyrimidines of the general formula I $$\underset{N}{\overset{N}{\bigg\langle}}\hspace{-2pt}=\hspace{-10pt}\underset{}{\overset{\overset{R_1}{|}}{\underset{}{\overset{}{\bigg\langle}}}}\hspace{-4pt}\underset{N-CH}{\overset{CO}{\underset{|}{\diagdown}}}\underset{R_3}{\overset{R_2}{\diagup}} \qquad (I)$$

wherein $R_1$ is $C_1$–$C_8$alkyl, $C_1$–$C_6$alkoxy, $C_1$–$C_4$alkoxy-$C_1$–$C_8$alkyl, $C_1$–$C_4$thioalkyl or halogen; phenyl or phenoxy, each unsubstituted or substituted by halogen, $C_1$–$C_4$alkyl, $C_1$–$C_4$haloalkyl, $C_1$–$C_4$carboxylalkyl, $C_1$–$C_4$haloalkoxy, $C_1$–$C_4$alkoxy, $C_1$–$C_4$haloalkylthio, cyano or nitro; $C_2$–$C_4$alkenyl or $C_2$–$C_4$alkynyl, or is $C_3$–$C_6$cycloalkyl which is unsubstituted or substituted by halogen or $C_1$–$C_4$alkyl, $R_2$ is $C_1$–$C_8$alkyl which is unsubstituted or substituted by halogen, cyano or $C_1$–$C_4$alkoxy; phenyl or $C_1$–$C_8$phenylalkyl, in each of which the phenyl nucleus is unsubstituted or substituted as defined for $R_1$; pyridyl, thienyl or furyl, in which the nucleus is unsubstituted or substituted in the same manner as phenyl as defined for $R_1$; or is pyranyl, dihydropyranyl, $C_3$–$C_7$cycloalkyl or $C_3$–$C_7$alkenyl, and $R_3$ is hydrogen or $C_1$–$C_8$alkyl and $R_2$ and $R_3$, together with the carbon atom to which they are attached, may form a $C_5$–$C_7$cycloalkyl radical.

Depending on the indicated number of carbon atoms, alkyl by itself or as moiety of another substituent, e.g. alkoxy, thioalkyl, alkoxyalkyl, haloalkoxy, carboxyalkyl, haloalkyl, haloalkylthio, comprises for example the following groups: methyl, ethyl, propyl, butyl, pentyl, hexyl, heptyl, octyl, and the isomers thereof, e.g. isopropyl, isobutyl, sec-butyl, tert-butyl, isopentyl, isoheptyl etc. Haloalkyl denotes a mono- or perhalogenated alkyl substituent, e.g. $CHCl_2$, $CHF_2$, $CH_2Cl$, $CCl_3$, $CH_2F$, $CH_2CH_2Cl$, $CHBr_2$ etc. Throughout this specification halogen denotes fluorine, chlorine, bromine or iodine, preferably fluorine, chlorine or bromine. Alkenyl is e.g. 1-propenyl, allyl, 1-butenyl, 2-butenyl, 3-butenyl or isoheptenyl. Alkynyl is e.g. ethynyl, 1-propynyl or propargyl. Depending on the number of carbon atoms, cycloalkyl is e.g. cyclopropyl, cyclobutyl, cyclopentyl, cyclohexyl or cycloheptyl.

Pyridyl denotes the radicals 3-pyridyl and 4-pyridyl, thienyl denotes the radicals 2-thienyl and 3-thienyl and furyl denotes the 2-furyl radical, pyranyl denotes the radicals 2H-2-pyranyl, 2H-3-pyranyl and 2H-4-pyranyl and dihydropyranyl denotes the radicals 3-(2H-5,6-dihydropyranyl) and 3-(2H-3,4-dihydropyranyl).

Acylamino-1,4-diazines are known from U.S. Pat. No. 4,441,912 as plant growth regulators.

The 5-acylaminopyrimidines (i.e. 5-acylamino-1,3-diazines) of the present invention are novel. These compounds of formula I are oils, resins or mainly crystalline solids which are stable at room temperature and have very valuable growth regulating properties. They can be used in agriculture or related fields preventively or curatively for regulating plant growth. The compounds of formula I of the invention are very well tolerated by cultivated plants.

One account of their pronounced growth regulating activity, those compounds are preferred, wherein $R_1$ is $C_2$–$C_4$alkyl, $R_2$ is phenyl which is unsubstituted or substituted by chlorine and $R_3$ is hydrogen.

Those compounds are particularly preferred, wherein $R_1$ is ethyl, propyl, isopropyl or tert-butyl and $R_2$ is 4-chlorophenyl or 2,4-dichlorophenyl.

The following individual compounds are particularly preferred:

N-(4-chlorobenzyl)-N-(pyrimidin-5-yl)propionamide,

N-(2,4-dichlorobenzyl)-N-(pyrimidin-5-yl)isobutyramide,

N-(4-chlorobenzyl)-N-(pyrimidin-5-yl)trimethylacetamide,

N-(2,4-dichlorobenzyl)-N-(pyrimidin-5-yl)trimethylacetamide,

N-(4-bromobenzyl)-N-(pyrimidin-5-yl)trimethylacetamide.

The 5-acylaminopyrimidines can be prepared by reacting a 5-aminopyrimidine of formula II, wherein $R_2$ and $R_3$ are as defined for formula I, with an acylating agent of formula IV:

$$\underset{N}{\overset{N}{\bigg\langle}}\hspace{-2pt}=\hspace{-10pt}\underset{}{\overset{}{\bigg\langle}}\hspace{-4pt}\underset{}{\overset{}{\diagdown}}NH-CH\underset{R_3}{\overset{R_2}{\diagup}} + \underset{Z}{\overset{R_1}{\diagdown}}C=O \longrightarrow I + ZH$$

II    IV

Suitable acylating agents of formula IV, wherein $R_1$ is as defined for formula I, are for example acid halides (Z=halogen) or acid anhydrides (Z=$R_1$COO—), wherein $R_1$ is as defined for formula I. The acylating agents of formula IV are generally known or can be prepared by known methods. When effecting acylation with an acid halide, an inert solvent and an acid acceptor can be employed. Suitable acid acceptors are tertiary amines which also advantageously act as solvents. When effecting acylation with an acid anhydride, an inert solvent and an acid acceptor can likewise be employed. In accordance with an advantageous embodiment, the acid forming in this reaction as by-product can be employed as solvent and the catalytic action of a mineral acid, if obtained, in particular of sulfuric acid, can be utilised.

The 5-aminopyrimidines of formula II are prepared by reducing azomethines (Schiff's bases) of formula III, wherein $R_2$ and $R_3$ are as defined for formula I, for example with the aid of sodium borohydride or by catalytic hydrogenation, in a suitable solvent, e.g. tetrahydrofuran or methanol:

$$\underset{N}{\overset{N}{\bigg\langle}}\hspace{-2pt}=\hspace{-10pt}\underset{}{\overset{}{\bigg\langle}}\hspace{-4pt}\underset{}{\overset{}{\diagdown}}N=C\underset{R_2}{\overset{R_1}{\diagup}} \xrightarrow{\text{reduction}} II$$

III

The azomethines of formula III are prepared by condensing the 5-aminopyrimidine of formula V with an oxo compound of formula VI, wherein $R_2$ and $R_3$ are as defined for formula I, in a suitable solvent, e.g. methanol:

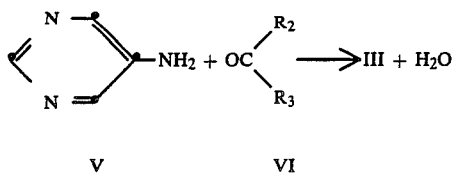

The 5-aminopyrimidines of formula II and the azomethines of formula III are novel and likewise constitute an object of the present invention.

The 5-aminopyrimidine of formula V is known from the literature (q.v. Whittacker, J. Chem. Soc. 1951, p. 1568).

Surprisingly, it has now been found that the novel compounds of formula I and compositions containing them are characterised in particular by their selective influence on plant metabolism. This selective influence on the physiological processes of plant development makes it possible to use the compounds of formula I for different purposes, especially for those in connection with increasing the yield of useful plants, with facilitating harvesting, and with labour-saving in measures taken in crops of cultivated plants.

Previous experience with growth regulators has shown that they are able to induce one or more different responses in the plants. These different responses depend substantially on the time of application, based on the state of development of the seed or plant, as well as on the concentrations of active ingredient applied to the plants or to the locus thereof and on the nature of application. Growth regulators should at all events induce positive responses in the cultivated plants in the desired manner.

Growth regulators may be used e.g. for inhibiting vegetative plant growth. Such a growth inhibition is of economic interest, inter alia, in respect of grasses, as the frequency of cutting in flower gardens, parks, sports fields or road shoulders can thereby be reduced. Of importance too is the inhibition of growth of herbaceous and ligneous plants on road shoulders and near transmission lines, or generally in areas in which strong growth is undesirable.

The use of growth regulators for inhibiting the growth in height of cereals is also important, as shortening the stalks diminishes or completely eliminates the danger of lodging before harvesting. In addition, growth regulators are able to bring about a strengthening of the stalks in crops of cereals, thereby also counteracting lodging.

Inhibition of the vegetative growth of many cultivated plants permits more plants to be sown in a crop area, so that a higher yield may be obtained per unit of area. A further mechanism of yield increase using growth regulators resides in the fact that nutrients are able increasingly to promote flower formation and fruiting, whereas vegetative growth is inhibited.

Growth regulators are also frequently able to promote vegetative growth. This is very beneficial when the vegetative parts of plants are to be harvested. However, promotion of vegetative growth can also result simultaneously in promotion of generative growth, so that e.g. more or larger fruit is formed.

Yield increases may also be obtained by influencing the plant metabolism without any visible changes in vegetative growth. Growth regulators can also induce a change in the composition of plants, so that the quality of the harvest produce is improved. For example, it is possible to increase the sugar content of sugar beet, sugar cane, pineapples and citrus fruit, or to increase the protein content of soybeans or cereals.

The use of growth regulators can lead to the formation of parthenocarpic fruit. The sex of blossoms can also be influenced. The production or flow of secondary plant substances can also be positively influenced by growth regulators, for example the stimulation of the flow of latex in rubber trees.

During plant growth, the development of side-shoots can also be promoted by the chemical interruption of apical dominance using growth regulators. This is of interest e.g. in the propagation of plant cuttings. However, it is also possible to inhibit the growth of side-shoots, e.g. in tobacco plants after decapitation in order to prevent the formation of side-shoots, and thus to promote leaf growth.

Influenced by growth regulators, the foliage of plants can be regulated in such a way that defoliation of the plants is achieved at a desired time. Such defoliation is useful for facilitating mechanical harvesting e.g. in vines or cotton, or for diminishing transpiration at a time when it is is desired to transplant the plants.

Premature fruit drop can be prevented by the use of growth regulators. However, it is also possible to promote fruit drop—e.g. in fruit crops—by means of chemical thinning up to a specific degree. Growth regulators can also be used for reducing the force necessary for detaching fruit at harvesting, so making possible mechanical harvesting of plants or facilitating manual harvesting.

With growth regulators it is also possible to speed up or delay the ripening of harvest products before or after harvesting. This is particularly advantageous, because a best possible accommodation to market requirements can thereby be achieved. In addition, growth regulators can often improve the colour of fruit. With the aid of growth regulators it is also possible to concentrate ripening at a particular time. The conditions are thus created for a complete mechanical harvesting of e.g. tobacco, tomatoes or coffee, or for manual harvesting, in only one single operation.

The application of growth regulators can also make it possible to influence the dormancy of seeds and buds of plants, i.e. the endogenic annual rhythm, so that plants, e.g. pineapples, or ornamentals in nurseries, germinate, sprout or blossom at a time when they would normally not tend to do so.

With growth regulators it is also possible to delay budding or the germination of seeds, e.g. in order to avoid damage by late frosts in areas endangered thereby. Conversely, root growth and/or the formation of shoots can be stimulated, so that growth may be restricted to a shorter period.

Growth regulators can also impart halophilic properties to cultivated plants. The conditions are thus created for cultivating plants in salty soil. Growth regulators can also induce resistance to frost and drought in plants.

Under the influence of growth regulators, the ageing (senescence) of plants or parts of plants can be inhibited or delayed. Such an action can be of great economic importance, as the storability of treated parts of plants or whole plants such as fruit, berries, vegetables, salads or ornamentals can be improved or prolonged after harvesting. Likewise, a substantial yield increase can be obtained by treating cultivated plants by prolonging the phase of photosynthetic activity.

A further important field of use for growth regulators is the inhibition of excessive growth of tropical cover crops. In tropical and subtropical monocultures, e.g. in palm tree plantations, cotton and maize fields etc., cover crops, especially species of leguminosae, are often planted together with the actual cultivated plants with the object of maintaining or improving the quality of the soil (prevention of desiccation, supplying nitrogen) and for preventing erosion. By applying the compounds of this invention it is possible to control the growth of these cover crops and so to keep the growth in height of these plants at a low level, thus ensuring healthy growth of the cultivated plants and the maintenance of favourable soil conditions.

The invention furthermore relates to a method of treating plants, which comprises applying thereto the compounds of the formula I or the novel compositions.

Target crops to be protected within the scope of the present invention comprise e.g. the following species of plants: cereals (wheat, barley, rye, oats, rice, sorghum and related crops); beet (sugar beet and fodder beet); pomes, drupes and soft fruit (apples, pears, plums, peaches, almonds, cherries, strawberries, rasberries and blackberries); leguminous plants (beans, lentils, peas, soybeans); oil plants (rape, mustard, poppy, olives, sunflowers, coconuts, castor oil plants, cocoa beans, groundnuts); cucumber plants (marrows, cucumber, melons); fibre plants (cotton, flex, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor); or plants such as maize, tobacco, nuts, coffee, sugar cane, tea, vines, hops, bananas and natural rubber plants, as well as ornamentals (composites), areas of grass, embankments or general low cover crops which counteract erosion or desication of the soil and are useful in cultures of trees and perennials (fruit plantations, hop plantations, maize fields, vineyards etc.).

The compounds of formula I are normally applied in the form of compositions and can be applied to the crop area or plant to be treated, simultaneously or in succession, with further compounds. These compounds can be both fertilisers or micronutrient donors or other preparations that influence plant growth. They can also be selective herbicides, insecticides, fungicides, bactericides, nematicides, mollusicides or mixtures of several of these compositions, if desired together with further carriers, surfactants or application-promoting adjuvants customarily employed in the art of formulation.

Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

A preferred method of applying a compound of formula I or an agrochemical composition which contains at least one of said compounds, is foliar application. The number of applications depends on the manner in which growth is influenced. However, the compounds of formula I can also penetrate the plant thrugh the roots via the soil (systemic action) by impregnating the locus of the plant with a liquid composition, or by applying the compounds in solid form to the soil, e.g. in granular form (soil application). The compounds of formula I may also be applied to seeds (coating) by impregnating the seeds either with a liquid formulation containing a compound of formula I, or by coating them with a solid formulation. In special cases, further types of application are also possible, e.g. selective treatment of the plant stems or buds.

The compounds of formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering, coating or pouring, are chosen in accordance with the intended objectives and the prevailing circumstances. Advantageous rates of application are normally from 10 g to 5 kg of active ingredient (a.i.) per hectare, preferably from 100 g to 2 kg a.i./ha, most preferably from 200 g to 600 g a.i./ha.

The formulations, i.e. the compositions, preparations or mixtures containing the compound (active ingredient) of formula I and, where appropriate, a solid or liquid adjuvant, are prepared in known manner, e.g. by intimately mixing and/or grinding the compounds of formula I with extenders, e.g. with solvents, solid carriers, and optionally surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as expoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Depending on the nature of the compound of formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications:

"McCutcheon's Detergents and Emulsifiers Annual", MC Publishing Corp., Ridgewood, N.J., 1979; Sisley and Wood, "Encyclopedia of Surface Active Agents", Chemical Publishing Co. Inc., New York, 1964.

The agrochemical compositions usually contain 0.1 to 99%, preferably 0.1 to 95%, of a compound of the formula I, 1 to 99%, of a solid or liquid adjuvant, and 0 to 25%, preferably 0.1 to 25%, of a surfactant.

Preferred formulations are composed in particular of the following constituents (% = percentage by weight):

| | |
|---|---|
| Solutions | |
| active ingredient | 5 to 95%, preferably 10 to 80% |
| solvent | 95 to 5%, preferably 90 to 0% |
| surfactant | 1 to 30%, preferably 2 to 20% |
| Emulsifiable concentrates | |
| active ingredient | 10 to 50%, preferably 10 to 40% |
| surfactant | 5 to 30%, preferably 10 to 20% |
| liquid carrrier | 20 to 95%, preferably 40 to 80% |
| Dusts | |
| active ingredient | 0.5 to 10%, preferably 2 to 8% |
| solid carrier | 99.5 to 90%, preferably 98 to 92% |
| Suspension concentrates | |
| active ingredient | 5 to 75%, preferably 10 to 50% |
| water | 94 to 25%, preferably 90 to 30% |
| surfactant | 1 to 40%, preferably 2 to 30% |
| Wettable powders | |
| active ingredient | 5 to 90%, preferably 10 to 80% most preferably 20 to 60% |
| surfactant | 0.5 to 20%, preferably 1 to 15% |
| solid carrier | 5 to 90%, preferably 30 to 70% |
| Granulates | |
| active ingredient | 0.5 to 30%, preferably 3 to 15% |
| solid carrier | 99.5 to 70%, preferably 97 to 85%. |

Whereas commercial products will be preferably formulated as concentrates, the end user will normally employ dilute formulations. The formulations can be diluted to a concentration as low as 0.001% of active ingredient.

The compositions may also contain further ingredients such as stabilisers, antifoams, viscosity regulators, binders, tackifiers, as well as fertilisers and other compounds for obtaining special effects.

Such agrochemical compsitions constitute an object of the present invention.

The invention is illustrated in more detail by the following non-limitative Examples.

PREPARATORY EXAMPLES

Example 1(a)

Preparation of N-(4-chlorobenzyl)-N-(pyrimidin-5-yl)trimethylacetamide (compound 1.001)

3.08 g (14 mmol) of N-(4-chlorobenzyl)-N-(pyrimidin-5-yl)amine are dissolved in 20 ml of pyridine and 0.2 g of p-dimethylaminopyridine and the solution is heated with stirring to 100° C. Over 30 minutes, 3.02 g (25 mmol) of trimethylacetyl chloride are added in portions to the solution. The reaction mixture is cooled to room temperature, diluted with 50 ml of ethyl acetate and strongly acidified with dilute sulfuric acid. Stirring is discontinued after 5 minutes and the layers are separated. After the phase separation, the solvent is evaporated off in vacuo at 80° C. from the lighter layer and the resultant residue is recrystallised from a mixture of 3 ml of toluene and 8 ml of cyclohexane. The resultant pure product melts at 122°–123° C., yield 37.2%. A further 43% of theory of N-(4-chlorobenzyl)-N-(pyrimidin-5-yl)trimethylacetamide are obtained by working up the mother liquor (column chromatography through silica gel; eluant: hexane/ethyl acetate (3:2)).

Example 1(b)

Preparation of N-(4-chlorobenzyl)-5-aminopyrimidine (compound 2.001)

With stirring, 1.89 g (50 mmol) of sodium borohydride are added in portions to a solution of 8.78 g (40 mmol) of N-(4-chlorobenzylidene)-5-aminopyrimidine in 70 ml of methanol over 30 minutes at room temperature. After a further 30 minutes, the reaction mixture is stirred in 200 ml of water and 50 ml of ethyl acetate and stirring is then discontinued. The upper layer is subsequently separated and dried over sodium sulfate. The solvent is evaporated off in vacuo at 60° C. from the filtrate and the residue is recrystallised from 25 ml of ethanol, affording 4.83 g (54.5% of theory) of N-(4-chlorobenzyl)-5-aminopyrimidine with a melting point of 128°-129° C. A further 1.99 g (22.5% of theory) of the product with a melting point of 128°-129° C. are obtained by evaporating the mother liquor and recrystallising the residue from ethanol.

Example 1(c)

Preparation of N-(4-chlorobenzylidene)-5-aminopyrimidine (compound 3.001)

5.71 g (60 mmol) of 5-aminopyrimidine and 9.84 g (70 mmol) of 4-chlorobenzaldehyde are mixed in 75 ml of methanol and the reaction mixture is heated to boiling point. The crystalline solid precipitated from the solution on cooling weighs 6.22 g (47.6% of theory) and melts at 138°-139° C. A further two fractions of the product—2.69 g (20.6% of theory, m.p.: 138°-139° C.) and 3.0 g (23.7% of theory, m.p.: 137°-138° C.)—can be isolated by recrystallising the distillation residue of the mother liquor from ethanol.

Example 2(a)

Preparation of N-(2,4-dichlorobenzyl)-N-(pyrimidin-5-yl)acetamide (compound 1.002)

2.80 g (11 mmol) of N-(2,4-dichlorobenzyl)-N-(pyrimidin-5-yl)amine are dissolved in 5 ml of glacial acetic acid and then 5 ml of acetic anhydride and 3 drops of concentrated sulfuric acid are added to the solution. With stirring, the reaction mixture is boiled under reflux for 1½ hours and subsequently cooled. 30 ml of chloroform are added to the mixture, the acetic acid is removed by extraction with water and the separated solution of chloroform is dried over sodium sulfate. The sodium sulfate is filtered off and the chloroform is then evaporated off in vacuo at 80° C. and the residue is recrystallised from a mixture of 5 ml of toluene and 5 ml of cyclohexane, affording 2.23 g (68.5% of theory) of N-(2,4-dichlorobenzyl)-N-(pyrimidin-5-yl)acetamide, m.p. 134°-136° C. A further 0.90 g (27.6% of theory) of pure product is obtained by purifying the product formed in the filtrate through a column of silica gel (eluant: ethyl acetate).

Example 2(b)

Preparation of N-(2,4-dichlorobenzyl)-5-aminopyrimidine (compound 2.002)

11.06 g (44 mmol) of N-(2,4-dichlorobenzylidene)-5-aminopyrimidine are stirred in 60 ml of methanol and 30 ml of dioxane and then 2.00 g (53 mmol) of sodium borohydride are added in portions to the mixture, whereupon the temperature rises from 20° to 50° C. and a solution forms which is stirred in water and chloroform. After drying the separated chloroform layer over Na$_2$SO$_4$, this solution is then concentrated by evaporation in vacuo and the residue is crystallised from a mixture of 30 ml of toluene and 5 ml of ethanol. The isolated product weighs 7.13 g (64% of theory) and melts at 104°-105° C. A further 3.22 g (28.9% of theory) of the product are obtained by purifying the evaporation residue of the mother liquor by column chromatography (in methyl acetate through silica gel) and working up as described above.

Example 2(c)

Preparation of N-(2,4-dichlorobenzylidene)-5-aminopyrimidine (compound 3.002)

A solution of 5.71 g (60 mmol) of 5-aminopyrimidine in 30 ml of methanol is stirred at room temperature in a solution of 11.55 g (66 mmol) of 2,4-dichlorobenzaldehyde in 30 ml of methanol and the solution thus formed is heated with stirring to boiling point, whereupon the resultant product crystallises. The crystalline product is filtered with suction at room temperature and dried. The N-(2,4-dichlorobenzylidene)-5-aminopyrimidine with a melting point of 189°-191° C. weighs 14.51 g (95.9% of theory).

The compounds listed in the following tables are prepared in analogous manner:

TABLE 1

Compounds of formula I

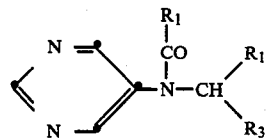

(I)

| Comp. | R$_1$ | R$_2$ | R$_3$ | Physical data |
|---|---|---|---|---|
| 1.001 | (CH$_3$)$_3$—C— | 4-Cl—C$_6$H$_4$— | H— | m.p. 122-123° C. |
| 1.002 | CH$_3$— | 2-Cl—4-Cl—C$_6$H$_3$— | H— | m.p. 134-136° C. |
| 1.003 | (CH$_3$)$_3$—C— | 2-Cl—4-Cl—C$_6$H$_3$— | H— | m.p. 107-108° C. |
| 1.004 | (CH$_3$)$_2$—CH— | 2-Cl—4-Cl—C$_6$H$_3$— | H— | m.p. 104-105° C. |
| 1.005 | C$_2$H$_5$— | 4-Cl—C$_6$H$_4$— | H— | m.p. 92-94° C. |
| 1.006 | (CH$_3$)$_3$—C— | 4-F—C$_6$H$_4$— | H— | m.p. 104-105° C. |
| 1.007 | (CH$_3$)$_3$—C— | 4-CH$_3$—C$_6$H$_4$— | H— | m.p. 145-146° C. |
| 1.008 | (CH$_3$)$_3$—C— | 3-CH$_3$—4-CH$_3$—C$_6$H$_3$— | H— | |
| 1.009 | (CH$_3$)$_3$—C— | 2-CH$_3$—4-CH$_3$—C$_6$H$_3$— | H— | |
| 1.010 | (CH$_3$)$_3$—C— | 2-Cl—C$_6$H$_4$— | H— | m.p. 100-102° C. |

TABLE 1-continued
Compounds of formula I

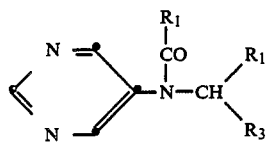 (I)

| Comp. | $R_1$ | $R_2$ | $R_3$ | Physical data |
|---|---|---|---|---|
| 1.011 | $(CH_3)_3$—C— | 2-Cl—3-Cl—$C_6H_3$— | H— | |
| 1.012 | $(CH_3)_3$—C— | $C_6H_5$— | H— | m.p. 106–107° C. |
| 1.013 | $(CH_3)_3$—C— | 3-$CF_3$—$C_6H_4$— | H— | m.p. 106–107° C. |
| 1.014 | $(CH_3)_3$—C— | 2-F—3-Cl—$C_6H_3$— | H— | |
| 1.015 | $(CH_3)_3$—C— | 2-Br—3-Cl—$C_6H_3$— | H— | |
| 1.016 | $(CH_3)_3$—C— | 2-Cl—4-Br—$C_6H_3$— | H— | |
| 1.017 | $(CH_3)_3$—C— | 4-Br—$C_6H_4$— | H— | m.p. 128–129° C. |
| 1.018 | 4-Cl—$C_6H_4$— | $C_2H_5$— | H— | |
| 1.019 | 4-Cl—$C_6H_4$— | $CH_3$—$CH_2$—$CH_2$— | H— | |
| 1.020 | 4-Cl—$C_6H_4$— | $(CH_3)_3C$— | H— | |
| 1.021 | 4-Cl—$C_6H_4$— | $(CH_3)_2CH$— | H— | |
| 1.022 | 2-Cl—4-Cl—$C_6H_3$— | $C_2H_5$— | H— | |
| 1.023 | 2-Cl—4-Cl—$C_6H_3$— | $CH_3$—$CH_2$—$CH_2$— | H— | |
| 1.024 | 2-Cl—4-Cl—$C_6H_3$— | $(CH_3)_3C$— | H— | |
| 1.025 | 2-Cl—4-Cl—$C_6H_3$— | $(CH_3)_2CH$— | H— | |
| 1.026 | 2-Cl—4-Cl—$C_6H_3$— | 4-Cl—$C_6H_4$— | H— | |
| 1.027 | 2-Cl—4-Cl—$C_6H_3$— | 2-Cl—4-Cl—$C_6H_3$— | H— | |
| 1.028 | $(CH_3)_3C$— | 4-Cl—$C_6H_4$—$CH_2O$— | H— | |
| 1.029 | $(CH_3)_3C$— | 4-F—$C_6H_4$—$CH_2O$— | H— | |
| 1.030 | $(CH_3)_3C$— | 2-Cl—4-Cl—$C_6H_3$—$CH_2O$— | H— | |
| 1.031 | $(CH_3)_3C$— | $C_6H_5$—$CH_2O$— | H— | |
| 1.032 | $(CH_3)_2CH$— | 4-Cl—$C_6H_4$—$CH_2O$— | H— | |
| 1.033 | $(CH_3)_2CH$— | 4-F—$C_6H_4$—$CH_2O$— | H— | |
| 1.034 | $(CH_3)_2CH$— | 2-Cl—4-Cl—$C_6H_3$—$CH_2O$— | H— | |
| 1.035 | $(CH_3)_2CH$— | $(CH_3)_3C$— | H— | |
| 1.036 | $(CH_3)_2CH$— | $C_2H_5$— | H— | |
| 1.037 | 4-Cl—$C_6H_4$— | 4-Cl—$C_6H_4$—$CH_2O$— | H— | |
| 1.038 | $(CH_3)_3C$— | 4-Cl—$C_6H_4$— | $CH_3$— | m.p. 133° C. |
| 1.039 | $(CH_3)_3C$— | $(CH_3)C$— | $CH_3$— | |
| 1.040 | $(CH_3)_3C$— | $C_2H_5$— | $CH_3$— | |
| 1.041 | $(CH_3)_3C$— | 4-Cl—$C_6H_4$—$CH_2O$— | $CH_3$— | |
| 1.042 | $(CH_3)_3C$— | 4-F—$C_6H_4$—$CH_2O$— | $CH_3$— | |
| 1.043 | $C_6H_4$— | $(CH_3)_3C$— | H— | |
| 1.044 | $C_6H_5$ | 4-Cl—$C_6H_4$— | H— | |
| 1.045 | cyclopropyl (CH$_2$–CH–CH$_2$) | 4-Cl—$C_6H_4$— | H— | |
| 1.046 | cyclopropyl (CH$_2$–CH–CH$_2$) | 2-Cl—4-Cl—$C_6H_3$— | H— | |
| 1.047 | cyclopropyl (CH$_2$–CH–CH$_2$) | $C_2H_5$— | H— | |
| 1.048 | cyclopropyl (CH$_2$–CH–CH$_2$) | $(CH_3)_3C$— | H— | |
| 1.049 | cyclopropyl (CH$_2$–CH–CH$_2$) | 4-F—$C_6H_4$— | H— | |
| 1.050 | 2-methylcyclopropyl (CH$_2$–CH–CH(CH$_3$)) | 4-Cl—$C_6H_4$— | H— | |

TABLE 1-continued

Compounds of formula I $$\text{(I)}$$

Structure: imidazole ring connected to C(=O)-N(R_1) where N is also bonded to CH(R_1)(R_3) and the imidazole carbon bears R_2 via C=N... (formula I as shown)

| Comp. | R_1 | R_2 | R_3 | Physical data |
|---|---|---|---|---|
| 1.051 | cyclohexyl (CH_2CH_2CH_2CH_2CH_2CH–) | 4-Cl—C_6H_4— | H— | |
| 1.052 | (CH_3)_3C— | 3-pyridyl | H— | m.p. 116–117° C. |
| 1.053 | (CH_3)_3C— | 4-pyridyl | H— | |
| 1.054 | (CH_3)_3C— | 2-methylfuran-5-yl | H— | m.p. 112–114° C. |
| 1.055 | (CH_3)_3C— | 2-methylthiophen-5-yl | H— | m.p. 75–77° C. |
| 1.056 | (CH_3)_3C— | thiophen-2-yl | H— | m.p. 92–93° C. |
| 1.057 | CH_3— | 2-Cl—4-Cl—C_6H_3— | H— | m.p. 134–136° C. |
| 1.058 | C(CH_3)_3— | 4-Cl—C_6H_4— | H— | m.p. 120–123° C. |
| 1.059 | (CH_3)_3C— | | (—CH_2—)_5 | m.p. 133–134° C. |
| 1.060 | Cl_2CH— | C_6H_5— | H— | m.p. 127–128° C. |
| 1.061 | Cl_2CH— | 2-Cl—6-Cl—C_6H_3— | H— | m.p. 148–149° C. |
| 1.062 | Cl_2CH— | 2-Cl—C_6H_4— | H— | m.p. 164–166° C. |
| 1.063 | (CH_3)_3C— | 4-(CH_3O)C_6H_4— | H | m.p. 106° C. |
| 1.064 | Cl_2CH | 3-pyridyl | H | m.p. 125–128° C. |
| 1.065 | (CH_3)_3C— | 4-chloro-2-(4-chlorophenoxy)phenyl | H— | m.p. 124–125° C. |
| 1.066 | Cl_2CH— | furan-2-yl | H— | m.p. 105–107° C. |

TABLE 1-continued

Compounds of formula I

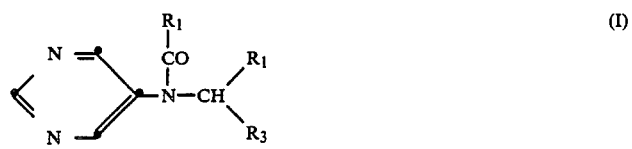

| Comp. | $R_1$ | $R_2$ | $R_3$ | Physical data |
|---|---|---|---|---|
| 1.067 | $(CH_3)_3C-$ | (2-methyl-3,6-dihydro-2H-pyran-ring) | $H-$ | m.p. 82–84° C. |
| 1.068 | $(CH_3)_3C-$ | $CH_3-(CH_2)_2-CH=C(C_2H_5-)-$ | $H-$ | m.p. 101–102° C. |
| 1.069 | $(CH_3)_3C-$ | $(-CH_2-)_6$ | | m.p. 127–129° C. |
| 1.070 | $(CH_3)_3C-$ | $2-Cl-6-Cl-C_6H_3-$ | $H-$ | m.p. 165–166° C. |
| 1.071 | $CH_2=C(C_2H_5)-$ | $C_6H_5$ | $H-$ | m.p. 76–77° C. |
| 1.072 | $CH_2=C(C_2H_5)-$ | $2-Cl-6-Cl-C_6H_3-$ | $H-$ | m.p. 115–116° C. |
| 1.073 | $4-Cl-C_6H_4-$ | (3-CF$_3$-phenyl ring) | $H-$ | m.p. 92–94° C. |
| 1.074 | $(CH_3)_3C-$ | $(CH_3)_3C-$ | $H-$ | m.p. 140–141° C. |
| 1.075 | $(CH_3)_3C-$ | (phenyl ring H) | $H-$ | m.p. 120–122° C. |
| 1.076 | $(CH_3)_3C-$ | $3-Cl-C_6H_4$ | $H-$ | m.p. 127–128° C. |
| 1.077 | $CH_3OCH_2-$ | $4-Cl-C_6H_4$ | H | m.p. 77–78° C. |
| 1.078 | $CH_3-CH(C_2H_5)-$ | $4-Cl-C_6H_4$ | H | m.p. 101° C. |

TABLE 2

Compounds of formula II

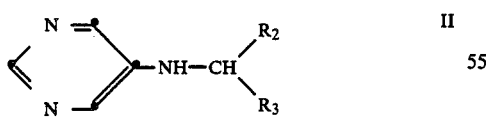

| Comp. | $R_2$ | $R_3$ | Physical data |
|---|---|---|---|
| 2.001 | H | $4-Cl-C_6H_4-$ | m.p. 128–129° C. |
| 2.002 | $H-$ | $2-Cl-4-Cl-C_6H_4-$ | m.p. 104–105° C. |
| 2.003 | $H-$ | $4-F-C_6H_4-$ | m.p. 125–126° C. |
| 2.004 | $H-$ | $4-CH_3-C_6H_4-$ | m.p. 142–143° C. |
| 2.005 | $H-$ | $3-CH_3-4-CH_3-C_6H_3-$ | |
| 2.006 | $H-$ | $3-CH_3-4-CH_3-C_6H_3-$ | |
| 2.007 | $H-$ | $2-CH_3-3-CH_3-C_6H_3-$ | |
| 2.008 | $H-$ | $2-Cl-C_6H_4-$ | m.p. 91–93° C. |
| 2.009 | $H-$ | $2-Cl-3-Cl-C_6H_3-$ | |
| 2.010 | $H-$ | $C_6H_5-$ | m.p. |

TABLE 2-continued

Compounds of formula II

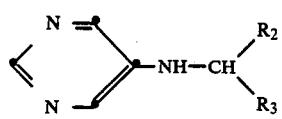   II

| Comp. | R₂ | R₃ | Physical data |
|---|---|---|---|
| 2.011 | H— | 3-CF₃—C₆H₄— | 107–109° C. m.p. 123–125° C. |
| 2.012 | H— | 2-F—4-Cl—C₆H₅— | |
| 2.013 | H— | 2-Br—4-Cl—C₆H₃— | |
| 2.014 | H— | 2-Cl—4-Br—C₆H₃— | |
| 2.015 | H— | 2-Br—C₆H₄— | |
| 2.016 | H— | C₂H₅— | |
| 2.017 | H— | CH₃—CH₂—CH₂— | |
| 2.018 | H— | (CH₃)₃C— | m.p. 193–195° C. |
| 2.019 | H— | (CH₃)₂CH— | |
| 2.020 | H— | 4-Cl—C₆H₄—CH₂O— | |
| 2.021 | H— | 4-F—C₆H₄—CH₂O— | |
| 2.022 | H— | 2-Cl—4-Cl—C₆H₃—CH₂O— | |
| 2.023 | H— | C₆H₅—CH₂O— | |
| 2.024 | CH₃— | 4-Cl—C₆H₄— | m.p. 157–159° C. |
| 2.025 | CH₃— | (CH₃)₃C— | |
| 2.026 | CH₃— | C₂H₅— | |
| 2.027 | CH₃— | 4-Cl—C₆H₄—CH₂O— | |
| 2.028 | CH₃— | 4-F—C₆H₄— | |
| 2.029 | CH₃— |  | |
| 2.030 | CH₃— | 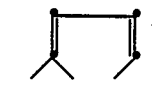 | |
| 2.031 | CH₃— |  | |
| 2.032 | CH₃— | 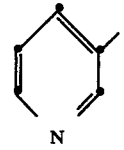 | |
| 2.033 | CH₃— |  | |
| 2.034 | H | 2,6-di-Cl—C₆H₃ | m.p. 144–146° C. |
| 2.035 | | —(CH₂)₅— | m.p. 114–116° C. |
| 2.036 | H | 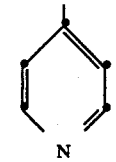 | m.p. 93–95° C. |
| 2.037 | H | —CH₂—(CH₂)₂—CH=C(C₂H₅)— | b.p. 10⁻² torr 112–116° C. |
| 2.038 | H |  | m.p. 111–113° C. |
| 2.039 | H |  | m.p. 135–137° C. |
| 2.040 | H | 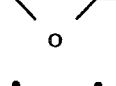 | m.p. 145–146° C. |
| 2.041 | H | 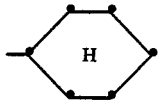 | m.p. 87–89° C. |
| 2.042 | H | 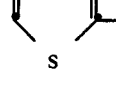 | m.p. 73–75° C. |
| 2.043 | H | 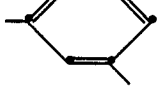 | m.p. 114–116° C. |
| 2.044 | H | —(CH₂)₆— | m.p. 83–85° C. |
| 2.045 | H | 4-Cl—C₆H₄— | m.p. 128–129° C. |
| 2.046 | H | 4-Br—C₆H₄— | m.p. 139–140° C. |
| 2.047 | H | 4-CH₃O—C₆H₄— | m.p. 166–168° C. |

TABLE 2-continued
Compounds of formula II

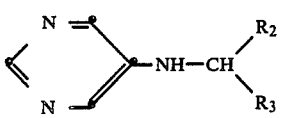

| Comp. | R₂ | R₃ | Physical data |
|---|---|---|---|
| 2.048 | H | 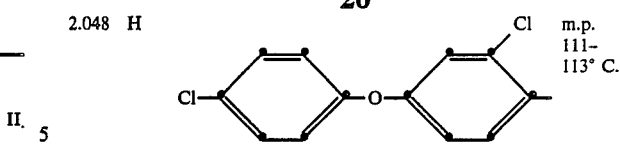 | m.p. 111–113° C. |

TABLE 3
Compounds of formula III

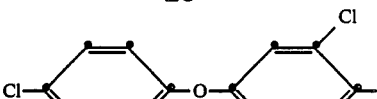

| Comp. | R₂ | R₃ | Physical data |
|---|---|---|---|
| 3.001 | H— | 4-Cl—C₆H₄— | m.p. 138–139° C. |
| 3.002 | H— | 2-Cl—4-Cl—C₆H₃— | m.p. 189–191° C. |
| 3.003 | H— | 4-F—C₆H₄— | m.p. 102–103° C. |
| 3.004 | H— | 4-CH₃—C₆H₄— | m.p. 74–76° C. |
| 3.005 | H— | 3-CH₃—4-CH₃—C₆H₄— | |
| 3.006 | H— | 2-Cl—C₆H₄— | m.p. 91–92° C. |
| 3.007 | H— | 2-Cl—3-Cl—C₆H₃— | |
| 3.008 | H— | C₆H₅— | m.p. 48–52° C. |
| 3.009 | H— | 3-CF₃—C₆H₄— | b.p. 135° C./10⁻² torr |
| 3.010 | H— | 2-F—4-Cl—C₆H₃— | |
| 3.011 | H— | 2-Br—4-Cl—C₆H₃— | |
| 3.012 | H— | 2-Cl—4-Br—C₆H₃— | |
| 3.013 | H— | 4-Br—C₆H₄— | m.p. 157–158° C. |
| 3.014 | H— | CH₃—CH₂—CH₂— | |
| 3.015 | H— | (CH₃)₃C— | b.p. 48° C./10⁻² torr |
| 3.016 | H— | (CH₃)₂CH— | |
| 3.017 | H— | 4-Cl—C₆H₄—CH₂O— | |
| 3.018 | H— | 4F—C₆H₄—CH₂O— | |
| 3.019 | H— | 2-Cl—4-Cl—C₆H₃—CH₂O— | |
| 3.020 | H— | C₆H₅—CH₂O— | |
| 3.021 | CH₃— | 4-Cl—C₆H₄— | m.p. 100–102° C. |
| 3.022 | CH₃— | (CH₃)₃C— | |
| 3.023 | CH₃— | C₂H₅— | |
| 3.024 | CH₃— | 4-Cl—C₆H₄—CH₂O— | |
| 3.025 | CH₃— | 4-F—C₆H₄— | |
| 3.026 | CH₃— |  | |
| 3.027 | CH₃— |  | |
| 3.028 | CH₃— |  | |
| 3.029 | CH₃— |  | |

TABLE 3-continued
Compounds of formula III
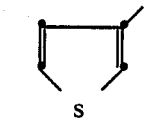 III
| Comp. | R₂ | R₃ | Physical data |
|---|---|---|---|
| 3.030 | CH₃— | 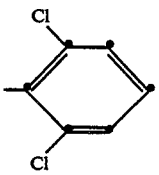 | |
| 3.031 | H | 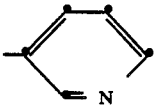 | m.p. 118–120° C. |
| 3.032 | H | —(CH₂)₅— | m.p. ca. 120° C./$10^{-2}$ torr |
| 3.033 | H | 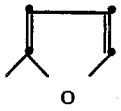 | m.p. 134–135° C. |
| 3.034 | H | CH₃—(CH₂)₂—CH=C(C₂H₅) | b.p. 100–103° C./$10^{-1}$ torr |
| 3.035 | H | 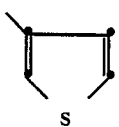 | m.p. 118–120° C. |
| 3.036 | H | 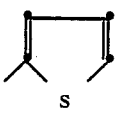 | m.p. 81–83° C. |
| 3.037 | H | 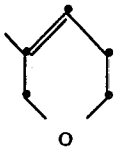 | m.p. 80–82° C. |
| 3.038 | H | 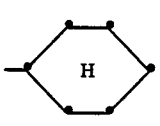 | m.p. 79–81° C. |
| 3.039 | H | 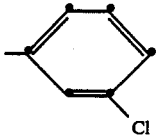 | viscous oil |
| 3.040 | H |  | m.p. 69–70° C. |
| 3.041 | H | —(CH₂)₆— | b.p. ca. 130° C./$10^{-2}$ torr |
| 3.042 | H | 2-Cl—4-Cl—C₆H₃— | m.p. 189–191° C. |
| 3.043 | H | 4-CH₃O—C₆H₄— | m.p. 128–131° C. |

TABLE 3-continued

Compounds of formula III

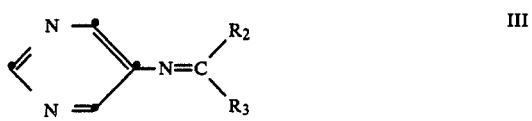

| Comp. | $R_2$ | $R_3$ | Physical data |
|---|---|---|---|
| 3.044 | H | Cl-C6H4-O-C6H4-Cl | m.p. 125–127° C. |

FORMULATION EXAMPLES

Example 3

Formulation Examples for liquid active ingredients of formula I (throughout, percentages are by weight)

| (a) Emulsifiable concentrates | (a) | (b) | (c) |
|---|---|---|---|
| active ingredient | 25% | 40% | 50% |
| calcium dodecylbenzenesulfonate | 5% | 8% | 5.8% |
| castor oil polyethylene glycol ether (36 moles of ethylene oxide) | 5% | — | — |
| tributylphenol polyethylene glycol ether (30 moles of ethylene oxide) | — | 12% | 4.2% |
| cyclohexanone | — | 15% | 20% |
| xylene mixture | 70% | 25% | 20% |

Emulsions of any required concentration can be produced from such concentrates by dilution with water.

| (b) Solutions | (a) | (b) | (c) | (d) |
|---|---|---|---|---|
| active ingredient | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20% | — | — |
| epoxidised coconut oil | — | — | 1% | 5% |
| petroleum distillate (boiling range 160–190°) | — | — | 94% | — |

These solutions are suitable for application in the form of microdrops.

| (c) Granulates | (a) | (b) |
|---|---|---|
| active ingredient | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| (d) Dusts | (a) | (b) |
|---|---|---|
| active ingredient | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

Example 4

Formulation examples for solid active ingredients of formula I (throughout, percentages are by weight)

| (a) Wettable powders | (a) | (b) |
|---|---|---|
| active ingredient | 25% | 60% |
| sodium lignosulfonate | 5% | 5% |
| sodium lauryl sulfate | 3% | — |
| sodium diisobutylnaphthalenesulfonate | — | 6% |
| octylphenol polyethylene glycol ether (7–8 moles of ethylene oxide) | — | 2% |
| highly dispersed silicic acid | 5% | 27% |
| kaolin | 67% | —% |

The active ingredient is thoroughly mixed with the adjuvants and the mixture is thoroughly ground in a suitable mill, affording wettable powders which can be diluted with water to give suspensions of the desired concentration.

| (b) Emulsifiable concentrate | |
|---|---|
| active ingredient | 10% |
| octylphenol polyethylene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| (c) Dusts | (a) | (b) |
|---|---|---|
| active ingredient | 5% | 8% |
| talcum | 95% | — |
| kaolin | — | 92% |

Ready-for-use dusts are obtained by mixing the active ingredient with the carrier, and grinding the mixture in a suitable mill.

| (d) Extruder granulate | |
|---|---|
| active ingredient | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| (e) Coated granulate | (a) |
|---|---|
| active ingredient | 3% |
| polyethylene glycol 200 | 3% |
| kaolin | 94% |

The finely ground active ingredient is uniformly applied, in a mixer, to the kaolin moistened with polyethylene glycol. Non-dusty coated granulates are obtained in this manner.

| (f) Suspension concentrate | |
|---|---|
| active ingredient | 40% |
| ethylene glycol | 10% |
| nonylphenol polyethylene glycol (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

Example 5

Growth inhibition of cereals

Summer barley (*Hordeum vulgare*) and summer rye (Secale) are sown in sterilised soil in plastic pots in a greenhouse and watered as required. The cereal shoots are sprayed about 21 days after sowing with an aqueous spray mixture of a compound of formula I. The concentration of test compound corresponds to 0.5 and 2.5 kg of active ingredient per hectare respectively. Evaluation of the growth of the cereals is made 10 and 21 days after application. A comparison with untreated controls shows that the growth of cereal plants treated with compounds of formula I is significantly reduced. The compounds of Table 1 prove particularly effective. Compounds 1.003 to 1.005 reduce the growth rate to less than 10%.

Example 6

Growth inhibition of grasses

Seeds of the grasses *Lolium perenne, Poa pratensis, Festuca ovina* and *Cynodon dactylon* are sown in plastic dishes filled with an earth/peat/sand mixture (6:3:1), in a greenhouse, and watered as required. The emergent grasses are cut back weekly to a height of about 4 cm, and about 50 days after sowing and 1 day after the last cut are sprayed with an aqueous spray mixture of a compound of formula I. The concentration of test compound corresponds to 0.5 and 2.5 kg of active ingredient 2.5 kg per hectare respectively. The growth of the grasses is evaluated 10 and 21 days after application. The compounds of Tables 1 effect a marked growth inhibition. Compound 1.003 effects a particularly marked growth inhibition and reduces new growth almost completely (growth rate about 10%).

Example 7

Yield increase of soybeans

Soybeans of the "Hark" variety are sown in plastic containers in an earth/peat/sand mixture (6:3:1). The containers are put into a climatic chamber and the plants develop to the 5–6 trefoil leaf stage after about 5 weeks by optimum control of temperature, light, fertiliser addition, and watering. The plants are then sprayed with an aqueous mixture of a compound of formula I until thoroughly wetted. The concentration of test compound corresponds to up to 500 ppm of active ingredient. Evaluation is made about 5 weeks after application. Compared with untreated controls, the compounds of the formula I markedly increase the number and weight of the harvested siliquae. The compounds of Table 1 prove particularly effective. In particular compounds 1.003 to 1.005 induce a yield increase of 5 to 12%.

Example 8

Growth inhibition of cover crops

Test plants of the varieties *Centrosema plumieri* and *Centrosema pubescens* are reared from cuttings in plastic pots filled with an earth/turf/sand mixture (1:1:1). After they have grown roots, the plants are transplanted into 9 cm pots and watered as required. For further growth the plants are then kept in a greenhouse at a day temperature of 27° C. and a night temperature of 21° C. The average light exposure is 14 hours (6000 lux) and the humidity is 70%. The plants are cut back to a height of about 15 cm and sprayed 7 days later with a spray mixture of the test compound (corresponding to a concentration of 0.3 and 3 kg a.i./ha respectively). Four weeks after application the growth of the treated plants is compared with that of untreated control plants which have been cut back. The test shows that the compounds of Table 1 effect a marked growth inhibition of the cover plants. In particular compounds 1.003 to 1.005 effect substantial growth inhibition and reduce the growth rate to 0 to 10%.

Example 9

Inhibition of senescence in cereal plants

Summer wheat of the "Svenno" variety is sown in pots with compost soil and reared without special climatic conditions. About 10 days after emergence, 10 to 12 cm primary leaves are cut off and put individually into the test tubes containing 10 ml of suspension of test compound (1.25 to 10 ppm of active ingredient). The test tubes are kept in a climatic room at 23° C. and 70% relative humidity and irradiated daily for an average of 14 hours (10,000 lux). Evaluation of inhibition of senescence is made 7 days later by comparing the degree of yellowing with still fresh, green leaves. This test shows that the compounds of Table 1 markedly inhibit the senescence of the test plants. In particular compounds 1.003 to 1.005 inhibit yellowing of the leaves by more than 80% during the test period.

Example 10

Growth inhibition of cereals

Barley and wheat are sown in sterilised soil in plastic pots ($\phi$12 cm) in a greenhouse and watered as required. The plants are thinned out to 10 per pot. The shoots are sprayed about 21 days after sowing with an aqueous spray mixture of a compound of formula I. The concentration of test compound is 0.3, 1.0 and 3.0 kg of active ingredient per hectare. Evaluation of the growth of the cereals is made 4 weeks after application.
The results are as follows:

| Treatment with compound | Concentration in kg a.i./ha | Crop | New growth after treatment | | % Dry weight % Height | Stem circumference of 10 plants |
|---|---|---|---|---|---|---|
| | | | Plant height | Dry weight | | |
| untreated | | | 100% | 100% | 1.0 | 100% |
| 1.017 | 0.3 | barley | 95% | 100% | 1.1 | 103% |
| 1.017 | 1.0 | barley | 81% | 70% | 0.9 | 106% |
| 1.017 | 3.0 | barley | 51% | 64% | 1.3 | 136% |
| 1.017 | 0.3 | wheat | 45% | 80% | 1.8 | 104% |
| 1.017 | 1.0 | wheat | 31% | 75% | 2.4 | 112% |
| 1.017 | 3.0 | wheat | 14% | 73% | 5.2 | 127% |
| 1.001 | 0.3 | barley | 44% | 99% | 2.3 | 102% |
| 1.001 | 1.0 | barley | 33% | 72% | 2.2 | 106% |
| 1.001 | 3.0 | barley | 19% | 60% | 3.2 | 122% |
| 1.001 | 0.3 | wheat | 82% | 79% | 1.0 | 112% |
| 1.001 | 1.0 | wheat | 55% | 59% | 1.1 | 115% |
| 1.001 | 3.0 | wheat | 29% | 52% | 1.8 | 124% |

Example 11

Growth inhibition of soybeans 7 soybean plants of the "Williams" variety are reared in plastic containers in an earth/peat/sand mixture (6:3:1). The plants are kept under hothouse conditions and watered as required.

The plants are sprayed 2 weeks after sowing with an aqueous spray mixture of a compound of formula I until thoroughly wetted. The concentration of test compound corresponds to 0.1, 0.5 and 1.5 kg of active ingredient per hectare. The new growth of the plants is determined 2 weeks after application and compared with that of untreated plants.

The results are as follows:

| Treatment with compound | Concentration in kg a.i./ha | Crop | New growth after treatment | | % Weight % Height |
|---|---|---|---|---|---|
| | | | Height | Fresh weight | |
| untreated | | | 100% | 100% | 1.0 |
| 1.003 | 0.1 | soybeans | 50% | 89% | 1.8 |
| 1.003 | 0.5 | soybeans | 27% | 83% | 3.1 |
| 1.003 | 1.5 | soybeans | 23% | 71% | 3.1 |
| 1.001 | 0.1 | soybeans | 100% | 100% | 1.0 |
| 1.001 | 0.5 | soybeans | 86% | 95% | 1.1 |
| 1.001 | 1.5 | soybenas | 76% | 95% | 1.3 |
| 1.017 | 0.1 | barley | 100% | 100% | 1.0 |
| 1.017 | 0.5 | barley | 81% | 94% | 1.2 |
| 1.017 | 1.5 | barley | 44% | 84% | 1.9 |

Example 12

Growth inhibition of grasses

A mixture comprising mainly grasses (*Poa pratensis, Dactylis glomerata, Lolium perenne, Festuca rubra, Festuca ovina, Cyonsurus cristatus, Agropyron repens* and *Promos inermis*) and a small amount of clover is sown in plastic containers filled with sterilised soil. The mixture is kept in a greenhouse and watered as required. The emergent grasses are cut back weekly to a height of about 4 cm and 8 to 9 weeks after sowing and 1 day after the last cut are sprayed with an aqueous spray mixture of a compound of formula I. The concentration of test compound corresponds to 0.3, 1.0 and 3.0 kg of active ingredient per hectare. The test compounds are evaluated 3 weeks after application.
The results are as follows:

| Treatment with compound | Concentration in kg a.i./ha | Crop | New growth after treatment (plant height) |
|---|---|---|---|
| untreated | | | 100% |
| 1.017 | 0.3 | mixture of grasses | 91% |
| 1.017 | 1.0 | mixture of grasses | 79% |
| 1.017 | 3.0 | mixture of grasses | 68% |
| 1.001 | 0.3 | mixture of grasses | 94% |
| 1.001 | 1.0 | mixture of grasses | 81% |
| 1.001 | 3.0 | mixture of grasses | 79% |

Example 13

Growth inhibition of cover crops

Cuttings of the test plants of the species *Centrosema pubescens* and *Psophocarpus palustris* with healthy roots are planted in plastic containers (φ12 cm) filled with an earth/peat mixture (1:3). The test plants are cut back to a height of about 15 cm and 7 days after cutting are sprayed with a spray mixture of the test compound (corresponding to a concentration of 0.3, 1 and 3 kg of active ingredient per hectare). 4 weeks after application the growth of the treated plants is compared with that of untreated control plants which have been cut back.
The results are as follows:

| Treatment with compound | Concentration in kg a.i./ha | Crop | New growth after treatment (plant height) |
|---|---|---|---|
| Unbehandelt | | | 100% |
| 1.001 | 0.3 | Centrosema pubescens | 100% |
| 1.001 | 1.0 | Centrosema pubescens | 90% |
| 1.001 | 3.0 | Centrosema pubescens | 20% |
| 1.001 | 0.3 | Psophocarpus palustris | 90% |
| 1.001 | 1.0 | Psophocarpus palustris | 30% |
| 1.001 | 3.0 | Psophocarpus palustris | 10% |

What is claimed is:
1. A 5-acylaminopyridine of the general formula I

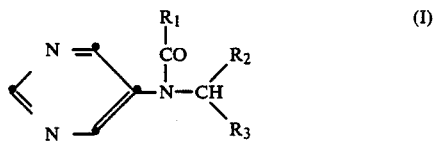

wherein
$R_1$ is $C_1$-$C_8$alkyl, $C_1$-$C_6$alkoxy, $C_1$-$C_4$alkoxy-$C_1$-$C_8$alkyl, or halogen; phenyl or phenoxy, each unsubstituted or substituted by halogen, $C_1$-$C_4$alkyl, $C_1$-$C_4$haloalkyl, $C_1$-$C_4$carboxylalkyl, $C_1$-$C_4$haloalkoxy, $C_1$-$C_4$alkoxy, $C_1$-$C_4$haloalkylthio, cyano or nitro; $C_2$-$C_4$alkenyl or $C_2$-$C_4$alkynyl, or is $C_3$-$C_6$cycloalkyl which is unsubstituted or substituted by halogen or $C_1$-$C_4$alkyl, $R_2$ is $C_1$-$C_8$alkyl which is unsubstituted or substituted by halogen, cyano or $C_1$-$C_4$alkoxy; phenyl or $C_1$-$C_8$phenylalkyl, in each of which the phenyl nucleus is unsubstituted or substituted as defined for R$_1$; pyridyl, thienyl or furyl, in which the nucleus is unsubstituted or substituted in the same manner as phenyl as defined for R$_1$; or is pyranyl, dihydropyranyl, C$_3$–C$_7$cycloalkyl or C$_3$–C$_7$alkenyl, and R$_3$ is hydrogen or C$_1$–C$_8$alkyl and R$_2$ and R$_3$, together with the carbon atom to which they are attached, may form a C$_5$–C$_7$cycloalkyl radical.

2. A compound according to claim 1, wherein R$_1$ is C$_1$–C$_8$alkyl, C$_1$–C$_6$alkoxy, C$_1$–C$_4$alkoxy-C$_1$–C$_8$alkyl, or halogen; phenyl or phenoxy, each unsubstituted or substituted by halogen, alkyl, haloalkyl, carboxylalkyl, haloalkoxy, haloalkylthio, cyano or nitro; C$_2$–C$_4$alkenyl, C$_2$–C$_4$alkynyl, or is C$_3$–C$_6$cycloalkyl which is unsubstituted or substituted by halogen or alkyl, R$_2$ is C$_1$–C$_8$alkyl which is unsubstiuted or substituted by halogen, cyano or alkoxy; phenyl or C$_1$–C$_8$-phenylalkyl, in each of which the phenyl nucleus is unsubstituted or substituted as defined for R$_1$; pyridyl, thienyl or furyl, in which the nucleus is unsubstituted or substituted in the same manner as phenyl as defined for R$_1$, and R$_3$ is hydrogen or C$_1$–C$_8$alkyl.

3. A compound according to claim 1, wherein R$_1$ is C$_2$–C$_4$alkyl, R$_2$ is phenyl which is unsubstituted or substituted by chlorine and R$_3$ is hydrogen.

4. A compound according to claim 1, wherein R$_1$ is ethyl, propyl, isopropyl or tert-butyl and R$_2$ is 4-chlorophenyl or 2,4-dichlorophenyl.

5. N-(4-Chlorobenzyl)-N-(pyrimidin-5-yl)propionamide according to claim 1.

6. N-(2,4-Dichlorobenzyl)-N-(pyrimidin-5-yl)isobutyramide according to claim 1.

7. N-(4-Chlorobenzyl)-N-(pyrimidin-5-yl)trimethylacetamide according to claim 1.

8. N-(2,4-Dichlorobenzyl)-N-(pyrimidin-5-yl)trimethylacetamide according to claim 1.

9. N-(4-Bromobenzyl)-N-(pyrimidin-5-yl)trimethylacetamide according to claim 1.

10. A composition for regulating plant growth, which composition contains as active ingredient at least one compound of formula I according to claim 1, together with carriers and/or other adjuvants.

11. A composition according to claim 10, which composition contains 0.1 to 99% of a compound of formula I, 99.9 to 1% of a solid or liquid adjuvant and 0 to 25% of a surfactant.

12. A composition according to claim 11, which composition contains 0.1 to 95% of a compound of formula I, 99.8 to 5% of a solid or liquid adjuvant and 0.1 to 25% of a surfactant.

13. A method of regulating plant growth, which method comprises applying to the plant or the locus thereof an effective amount of a compound of formula I as defined in claim 1.

14. A method according to claim 13 of inhibiting growth in order to increase resistance to lodging and shorten the stalks in crops of cereals.

15. A method according to claim 14, wherein the cereals are oats, wheat, barley or rye.

16. A method according to claim 13 of inhibiting the growth of grasses.

17. A method according to claim 13 of regulating the growth of legumes in order to increase yield.

18. A method according to claim 17, wherein the legumes are soybeans.

* * * * *